(12) United States Patent
Grinstein et al.

(10) Patent No.: US 9,021,878 B2
(45) Date of Patent: May 5, 2015

(54) FLOW RATE METER

(75) Inventors: Mor Grinstein, Modi'in (IL); Jack Yehoshua Mantinband, Efrata (IL); Shmuel Bentov, D. N. HaElla (IL); Michael Adler, Kfar Vradim (IL)

(73) Assignee: Renalsense Ltd., Jerusalem (IL)

( * ) Notice: Subject to any disclaimer, the term of this patent is extended or adjusted under 35 U.S.C. 154(b) by 323 days.

(21) Appl. No.: 13/642,602

(22) PCT Filed: Apr. 4, 2011

(86) PCT No.: PCT/IL2011/000289
§ 371 (c)(1),
(2), (4) Date: Oct. 22, 2012

(87) PCT Pub. No.: WO2011/138774
PCT Pub. Date: Nov. 10, 2011

(65) Prior Publication Data
US 2013/0041234 A1 Feb. 14, 2013

(30) Foreign Application Priority Data
May 3, 2010 (IL) .......................................... 205614

(51) Int. Cl.
*G01F 1/684* (2006.01)
*G01F 23/26* (2006.01)
*A61B 5/20* (2006.01)
*G01F 1/00* (2006.01)

(52) U.S. Cl.
CPC .............. *G01F 23/266* (2013.01); *A61B 5/208* (2013.01); *G01F 1/684* (2013.01); *A61B 2562/0271* (2013.01); *G01F 1/007* (2013.01)

(58) Field of Classification Search
CPC .......... G01F 1/684; G01F 1/696; G01F 5/00; G01F 5/005; G01F 1/6842
USPC .................... 73/204.11, 203, 202.5
See application file for complete search history.

(56) References Cited

U.S. PATENT DOCUMENTS

| 5,062,304 A | 11/1991 | Van Buskirk et al. |
| 6,536,273 B2 | 3/2003 | Schrittenlacher |
| 2006/0081045 A1 | 4/2006 | Robertson |
| 2009/0314101 A1 | 12/2009 | Levine |
| 2013/0041234 A1* | 2/2013 | Grinstein et al. ............. 600/301 |

FOREIGN PATENT DOCUMENTS

| WO | 99/06800 A1 | 2/1999 |
| WO | 2004100788 A1 | 11/2004 |
| WO | 2009064984 A2 | 5/2009 |

OTHER PUBLICATIONS

WIPO IPRP of corresponding PCT application, mailed Aug. 30, 2011 (7 pages).

* cited by examiner

*Primary Examiner* — Jewel V Thompson
(74) *Attorney, Agent, or Firm* — Roach Brown McCarthy & Gruber, P.C.; Kevin D. McCarthy (57) ABSTRACT

The present invention is flow rate meters which are able to accurately measure the volumetric rate of flow of a liquid through a conduit without requiring foreknowledge of the physicochemical characteristics of the liquid, e.g., for the purpose of calibration of the thermal mass flow rate. One application of the flow meters of the invention is to incorporate them in a system for measuring the flow rate of urine excreted by a catheterized patient. The invention also provides methods for using the flow rate meters.

15 Claims, 8 Drawing Sheets

FLOW RATE METER

FIELD OF THE INVENTION

The present invention relates to the field of flow rate meters. Specifically, the invention relates to flow rate meters which enable the accurate determination of the volumetric flow rate of a liquid.

BACKGROUND OF THE INVENTION

Flow measurement is important in many fields. For example, many industrial processes require measurement of flow through various conduits in order to control the process appropriately. Other uses requiring measurement of a liquid or gas include delivery of a product to a consumer, such as gas, oil, and water. In the medical field, liquid measurement is sometimes applied to a patient's urine output.

Most flow measurement systems rely upon various assumptions regarding the properties of the liquid to be measured and will not work or must be adjusted to cope with deviations from the assumed properties. For example, one well-known technique applies thermal transfer principles applying King's Law to determine the flow rate. With this approach, the thermal properties of the liquid to be measured must be known in advance.

Thermal transfer flow meters typically measure flow continuously using a heating element and two temperature sensors (one upstream & one downstream from, or adjacent to, the heater). By measuring the temperature differential between the two thermometers, the flow is calculated. Alternatively, the temperature is kept constant at the heater and the energy required to do so is monitored, from which the flow can be calculated.

Figure 1:
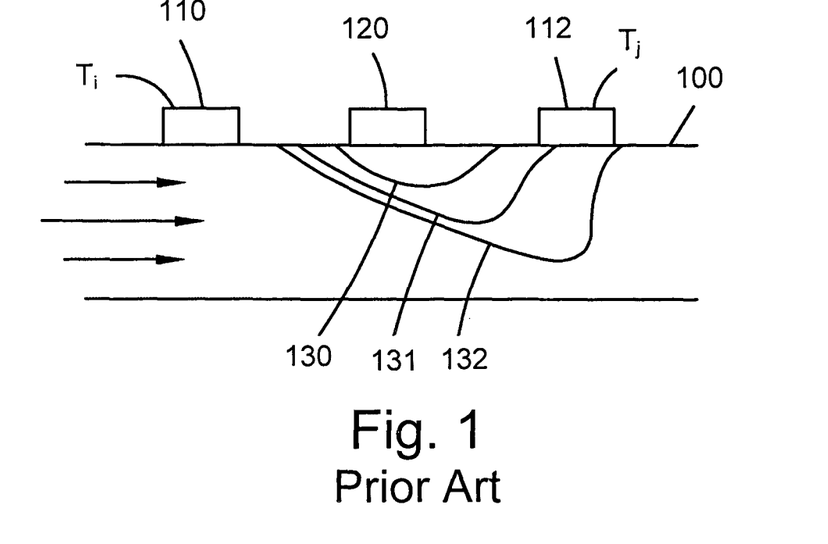
FIG. 1 schematically shows the basic arrangement of a prior art thermal transfer flow meter.

FIG. 1 schematically shows the basic arrangement of a prior art thermal mass flow meter. A liquid flows through a tube 100 in a direction indicated by the arrows. At some location in wall of the tube is placed heating element 120 with temperature sensor 110, which measures temperature $T_i$, and temperature sensor 112, which measures temperature $T_j$, located respectively upstream and downstream of heater 120. Isothermal lines 130, 131, and 132 symbolically show the temperature distribution as a result of the power input to the heating element, where the $T_{130} > T_{131} > T_{132}$.

The calculation for determining the flow rate is according to the formula:

$$W = Q/t = \rho \cdot \dot{V} \cdot C_p \cdot (T_j - T_i) \quad \text{equation 1}$$

Solving for $\dot{V}$:

$$\dot{V} = \frac{W}{\rho \cdot C_p \cdot (T_j - T_i)} \quad \text{equation 2}$$

And noting that $$W = I \cdot v$$

And substituting, yields $$\dot{V} = \frac{I \cdot v}{\rho \cdot C_p \cdot \Delta T} \quad \text{equation 3}$$

wherein the symbols used herein are defined in the following table:

| Symbol | Meaning | Units |
|---|---|---|
| V | Volume | [l] Liters |
| $\dot{V}$ | Volumetric Flow (volume/time) | $\left[\frac{l}{\min}\right]$ Liters/minute |
| Q | Energy, work | [J] Joules |
| P | Power | [J/sec] Joules/second |
| $\rho$ | Density | $\left[\frac{g}{l}\right]$ grams/liter |
| $C_p$ | Specific Heat Capacity (under constant pressure) | $\left[\frac{J}{g \cdot {}^\circ C.}\right]$ Joules/(gram·° C.) |
| T | Temperature | [° C.] degrees Celsius |
| $T_i$ | Temperature of liquid before the heater (upstream) | [° C.] degrees Celsius |
| $T_j$ | Temperature of liquid after or at the heater (downstream) | [° C.] degrees Celsius |
| I | Current | [A] Amperes |
| v | Electric potential | [v] Volts |
| $\Delta T$ | Temperature Difference $T_j - T_i$ | [° C.] degrees Celsius |
| t | Time | [s] seconds |

A related type of thermal transfer flow meter, known, inter alia, as a constant temperature flow meter, uses a similar arrangement to that shown in FIG. 1 with the exception that temperature sensor 112 is adjacent to, or integral with heating element 120. In this configuration, the heating element 120 is heated to a set constant differential temperature $T_j$ (as measured by sensor 112) above the temperature $T_i$ measured by sensor 110. As the flow varies, the amount of heat carried away by the flow varies. The temperature of heater 120 is kept constant by adjusting the current (assuming constant Voltage) applied thereto. The variation of the current required (I) to maintain a constant temperature differential $\Delta T$ provides a means to calculate the flow, as shown in equation 3.

As can be seen above, in order to accurately measure the flow rate using a thermal transfer flow meter, the density and the heat capacity of the measured liquid must be accurately known.

In some applications, there is no a priori knowledge of the liquid's properties, e.g. heat capacity and density. Some liquids can have varying properties—for example, urine is a liquid whose constituent components can vary from person to person, and, for a single person, can vary over time. As another example, milk can have varying fat content. In some applications, such as at a fuel terminal the same pipe may be used to transfer different types of fuel or gas or even sometimes either intentionally or unintentionally mixtures of gas and liquid products. In all of these situations, the readings of conventional thermal flow meters will be inaccurate and to improve the results the flow meters must be recalibrated on the basis of either assumptions that must be made about the properties of the liquid or empirical measurements.

In some cases, urine of bedside patients is measured manually, where urine flows along a catheter to a urine collection container and hospital personnel visually estimate the patient's urine output (ml/h) from the urine collection container. In practice, this arrangement is laborious and inaccurate, since hospital personnel must manually determine the amount of hourly urine and the dynamic nature of critical care settings makes it difficult to adhere to timely measurement. A simple, easy-to-use solution for measuring urine flow is needed to assist in accurate and timely measurement of urine output.

A brief understanding of related prior art can be gained from U.S. Pat. No. 6,536,273, which discloses a thermal flow rate sensor that can be used with liquids of variable composition. The sensor comprises two elements: a conventional thermal flow sensor and a thermal-conductivity measuring cell. The thermal-conductivity measuring cell is used to determine the composition of the liquid and the results of measurements made from this cell are combined with other calibration measurements to correct the measurements made by the flow sensor for the properties of the liquid.

It is therefore an object of the invention to provide simple, cost-effective, and accurate flow rate meters, which enable measuring the flow rate of a liquid without knowing beforehand the (possibly dynamic) physicochemical characteristics of liquid being measured.

It is another object of the invention to provide medical systems comprising the flow rate meters of the invention which enables monitoring the flow rate of a biological liquid from a patient.

It is a further object of the invention to provide a method for determining the flow rate of a liquid without knowing the possibly dynamic physicochemical properties of the tested liquid beforehand.

Further purposes and advantages of this invention will appear as the description proceeds.

SUMMARY OF THE INVENTION

In a first aspect the invention is an apparatus for measuring the volumetric rate of flow of a liquid through a conduit. The apparatus comprises the following components:
  a) a section of the conduit adapted to form at least one chamber in which a known volume of the liquid can be isolated and either held stationary or in which the velocity of the liquid is reduced significantly in relation to its velocity in the sections of the conduit on either end of the chamber;
  b) at least one heating or cooling element adapted to add or subtract a known quantity of heat to or from the isolated volume of liquid; and
  c) at least one temperature sensor adapted to measure the instantaneous temperature of the liquid;

At least one of the heating or cooling elements and at least one of the temperature sensors is in thermal contact with the liquid in the chamber; and the components of the apparatus are configured to allow the volumetric flow rate to be determined directly, by using only the measurements of the instantaneous temperature, the known volume of liquid, and one of either the known quantities of heat or a measured amount of time that elapses between the measurement of two specific instantaneous values of temperature.

Embodiments of the apparatus of the invention comprise a control system that comprises at least one of the following components: a processor, input means, memory units, display devices, and output means. The components of the control system are configured to carry out at least one of the following:
  a) to activate at least one valve located in the conduit at a location at which it can be used to divert a known volume of liquid flowing in the conduit into the chamber and/or to hold the known volume of liquid stationary;
  b) to activate at least one heating or cooling element;
  c) to receive data from temperature sensors and other types of sensors or meters that are present in the apparatus;
  d) to use the received data to determine the volumetric flow rate;
  e) to store and display to a user information related to the operation of the apparatus and the properties of the liquid that are measured or determined by components of the apparatus;
  f) to send instantaneous or historical values of measured temperatures and other information relative to the liquid and the apparatus to remote locations;
  g) to send signals that can be used as input to other systems; and
  h) to send alarms if there are predetermined changes in the flow rate or other measured properties of the liquid.

In embodiments of the apparatus of the invention the section of the conduit adapted to form at least one chamber is adapted in at least one of the following ways:
  a) by placing two valves in the conduit spaced apart by such a distance that the volume of the interior of the conduit between them defines the chamber;
  b) by splitting the conduit into at least two sub-conduits that are hermetically attached at their upstream and downstream ends to the conduit and providing a mechanism for managing the flow of liquid through the sub-conduits;
  c) by providing an inner chamber held in position inside the conduit by one or more supporting members and a piston located upstream of the inner chamber inside the conduit, wherein the piston is a solid cylinder with a coaxial hole bored through its center and the inner chamber is hollow and is closed on the upstream side with the exception of a coaxial entrance hole that is either open or blocked by a valve, which is activated by contact with the piston; and
  d) by providing a conduit comprising a small cross section segment followed by a large cross section segment which is followed in turn by a second small cross section segment.

In embodiments of the apparatus comprising sub-conduits at least one of the sub-conduits may comprise sensors that are in contact with liquid flowing through or trapped in the sub-conduit and that are adapted to measure at least one of the following properties of the liquid: electrical conductivity, osmolarity, osmolality, pH, biomarkers, electrolytes, specific gravity, specific density, conductivity, presence and concentration of: creatinine, urea, uric acid, white blood cells, red blood cells, glucose, ketones, number/concentration of ions.

Embodiments of the apparatus of the invention may comprise at least one of:
  a) a bubble trap located upstream of the measurement location;
  b) a gas-permeable membrane located upstream of the measurement location;
  c) a check valve located downstream of the measurement location; and
  d) a check valve located upstream of the measurement location.

Embodiments of the apparatus of the invention may be adapted to be either connected to or an integral part of a catheter or a drainage tube leading from a patient. In embodiments of the invention urine flows through the catheter or drainage tube and the control system of the apparatus is adapted to monitor the urine temperature and to send an alarm if changes occur that exceed a predetermined rate.

In a second aspect the invention is a method for measuring the volumetric rate of flow of a liquid through a conduit. The method comprises the following steps:

a) modifying a section of the conduit to form a chamber in which a known volume of the liquid can be isolated and either held stationary or in which the velocity of the liquid is reduced significantly in relation to its velocity in the sections of the conduit on either end of the chamber;

b) isolating the known volume of liquid in the chamber;

c) reading the temperature from a temperature sensor in thermal contact with the liquid in the chamber to measure an initial temperature of the liquid;

d) activating a heating or cooling element in thermal contact with the liquid in the chamber to add or subtract a known quantity of heat to or from the isolated volume of liquid;

e) reading the temperature from a temperature sensor in thermal contact with the liquid in the chamber to measure a final temperature of the liquid after the known quantity of heat has been added to or subtracted from the isolated volume of liquid;

f) determining the value of an aggregate coefficient from the known volume of the liquid, the known quantity of heat, and the difference between the initial and the final temperatures;

g) activating a thermal flow meter to measure the thermal flow rate;

h) determining the volumetric flow rate from the measured quantity of heat, the value of the aggregate coefficient, and the difference in the temperatures measured by the first and second temperature sensors at the end of the period of time.

In embodiments of the method of the invention the thermal flow rate is measured by:

a) activating a heating or cooling element in thermal contact with the flowing liquid at a location either in the chamber or at another location in the conduit to add to or subtract heat from the flowing liquid;

b) activating simultaneously with the activation of the heating or cooling element a first temperature sensor in thermal contact with the flowing liquid located upstream of the heating or cooling element and a second temperature sensor in thermal contact with the flowing liquid located downstream of the heating or cooling element;

c) measuring the quantity of heat added to or subtracted from the flowing liquid during a period of time;

d) determining the thermal flow rate from the measured quantity of heat and the difference in the temperatures measured by the first and second temperature sensors at the end of the period of time.

In embodiments of the method of the invention the thermal flow rate is measured by:

a) activating a heating or cooling element in thermal contact with the flowing liquid at a location either in the chamber or at another location in the conduit to add to or subtract heat from the flowing liquid;

b) activating simultaneously with the activation of the heating or cooling element a temperature sensor in thermal contact with the flowing liquid and adjacent to or integral to the heating or cooling element;

c) measuring the initial instantaneous temperature measure by the temperature sensor when it is activated;

d) allowing the instantaneous temperature measured by the temperature sensor to rise or fall until a predetermined temperature differential between the initial temperature and the instantaneous temperature is measured;

e) varying and measuring the amount of energy supplied to the heating or cooling element while maintaining the instantaneous temperature measured by the temperature at the temperature differential;

f) determining the quantity of heat added to or subtracted from the flowing liquid during a period of time from the measured amount of energy;

g) determining the thermal flow rate from the measured quantity of heat.

In embodiments of the method of the invention step c through step e and step g are carried out simultaneously in different sections of the conduit.

In embodiments of the method of the invention in step d the heating or cooling element is activated and the amount of heat added to or subtracted from the isolated volume of liquid is measured, in step e the temperature is read from the temperature sensor to determine when a predetermined final temperature is reached at which point the heating or cooling element is deactivated, and in step f the value of the aggregate coefficient is determined from the known volume of liquid, the measured quantity of heat, and the predetermined difference between the initial and the final temperatures.

In embodiments of the method of the invention steps d through h are replaced by the following steps:

d') activating a heating or cooling element in thermal contact with the liquid in the chamber to add or subtract heat to or from the isolated volume of liquid;

e') reading the temperature from a temperature sensor in thermal contact with the liquid in the chamber to measure the instantaneous temperature of the liquid while the quantity of heat is being added to or subtracted from the isolated volume of liquid;

f') deactivating the heating or cooling element when the temperature of the liquid reaches a final temperature different from the initial temperature;

g') allowing fresh liquid to flow through the chamber and activating a timer simultaneously with the time at which fresh liquid flow is initiated;

h') measuring the period of time that elapses until the temperature of the liquid in the chamber shifts from the final temperature back to a threshold value of temperature; and i') determining the volumetric flow rate from the known volume of the liquid and the measured period of time.

In embodiments of the method of the invention the method is adapted to measure the volumetric flow of a liquid through a catheter or a drainage tube leading from a patient. In some of these embodiments the liquid is urine.

BRIEF DESCRIPTION OF THE DRAWINGS

The above and other characteristics and advantages of the invention will be more readily apparent through the following examples, and with reference to the appended drawings, wherein.

DETAILED DESCRIPTION OF PREFERRED EMBODIMENTS

The present invention is flow rate meters which are able to accurately measure the volumetric flow rate of a liquid without requiring foreknowledge of the physicochemical characteristics of the liquid, e.g., for the purpose of calibration of the thermal mass flow rate. One application of the flow meters of the invention is to incorporate them in a system for measuring the flow rate of urine excreted by a catheterized patient. Other applications also exist and are included within the scope of this invention.

Consider now the heat capacity $C_p$ of the liquid flowing in a conduit. $C_p$ is $$C_p = \frac{Q}{\rho V \Delta T}$$

which can be rearranged to yield:

$$\rho \cdot C_p = \frac{Q}{V \Delta T}$$

We now define an aggregate coefficient $\gamma$, which represents the liquid properties.

$$\gamma = \rho \cdot C_p$$

Substituting $\gamma$ for $\rho \cdot C_p$, we have:

$$y = \frac{Q}{V \Delta T} \qquad \text{equation 4}$$

From equation 4 it can be appreciated that if:
a known volume V of the liquid is isolated in a cell containing a heating element and temperature sensor; and
the heat input Q to the cell is known either though measurement or by dosing; and
the change in temperature $\Delta T$ is known by measurement;
then sufficient information is available to determine $\gamma$ without knowing the density or the specific heat capacity of the measured liquid individually.

We now substitute in equation 3 to obtain:

$$\dot{V} = \frac{I \cdot v}{y \cdot \Delta T} \qquad \text{equation 5}$$

The values of I, v, and $\Delta T$ can be measured using a thermal flow meter as described with respect to FIG. 1. A known volume of the liquid can be isolated and measurements performed to measure the variable properties of the liquid flowing in a conduit. i.e. y.

According to an embodiment of the invention, the apparatus is configured such that a portion of the conduit through which the liquid flows is adapted to allow part of the stream of liquid to be split off from the main stream and to enter a chamber that can be closed, thereby allowing determination of $\gamma$. At the same time the liquid can continue flowing through the conduit and measurements can be made on the flowing liquid to obtain the rest of the data needed as input to equation 5. Alternatively, the chamber can be closed to measure the value of $\gamma$ immediately after which the chamber is opened allowing measurements to be made on the flowing liquid to obtain the rest of the data needed using the same heating element and temperature sensors used to measure $\gamma$.

It is important to realize that the method of the invention allows the actual value of the flow rate $\dot{V}$ to be determined directly using only measured parameters. This is as opposed to prior art methods of determining the mass flow rate that depend on look-up tables, coefficients of a polynomial defining a correlation curve, or similar sources of information to provide values based upon the density and specific heat capacity of the assumed composition of the liquid and typically derived by individual empirical calibration of the flow rate meter with the liquid of interest.

The method of the invention also allows for the automatic selection of an appropriate set of correlation data to be applied based upon the measured value of $\gamma$.

It is noted that heat capacity is an intrinsic property of the liquid under consideration. This property also varies with the pressure and temperature of the liquid, as well as its volume. When dealing with water, for example, the increase in volume is negligible. The coefficient of thermal expansion (CTE) for pure water at 20° C. is 207×10−6 (0.000207; therefore if the temperature is raised by 10° C., the volume change is about 0.00207, which is about 0.2%. Thus, the method of the invention holds true for water and other liquids, e.g. urine, with negligible CTE. Similarly, the changes in $C_p$ for variations of temperature and pressure over appropriately chosen ranges are negligible.

Figure 2:
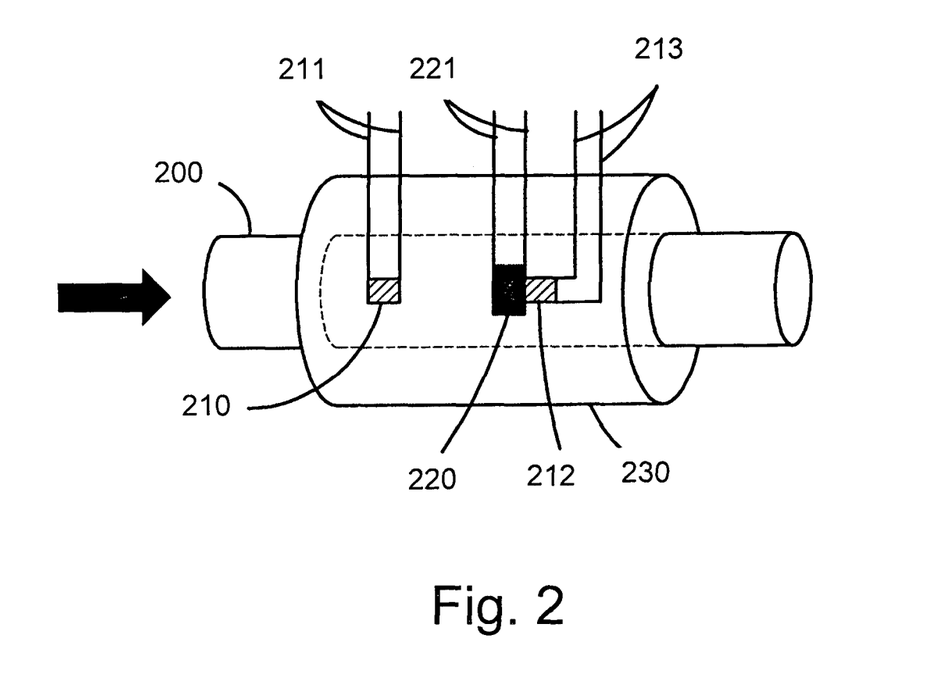
FIG. 2 schematically shows a section of conduit comprising components used for measuring the flow of a liquid flowing through it using thermal transfer techniques.

FIG. 2 schematically shows a section of conduit 200 (e.g., tubing or pipe) comprising components used for measuring the thermal mass flow of a liquid flowing through it in the direction indicated by the arrow. A temperature sensor 210 is located upstream of a heating element 220. The temperature measured by sensor 210 can be read out to a control or display unit via the leads 211. Heating element 220 is located inside conduit 200 inserted directly into the flowing liquid or on a heat-conductive portion of wall of the conduit. Electric power is supplied to heating element 220 by applying a voltage via the leads 221. Adjacent to heating element 220 is a second temperature sensor 212 that measures the temperature of the liquid downstream of heating element 220. The temperature measured by sensor 212 is read out via the leads 213. Preferably the section of conduit that contains heating element 220 and temperature sensors 210,212 is thermally isolated from the surroundings using insulation 230.

Herein the various embodiments of the apparatus are generally described as comprising an electrical heating element, but the invention is not to be limited in this way. Alternate sources of heat can be used to raise the temperature of the liquid, for example ultrasound or radio frequency or other electromagnetic energy. In all embodiments of the invention described herein, instead of using a heating element to raise the temperature of the liquid for purposes of making the measurements equivalent results can be obtained by using a cooling element to lower the temperature of the liquid. Therefore, herein the use of terms such as "heating element" are to be understood as applying equally to "cooling elements" and vice versa. Cooling of the liquid at the location of the measurements can be accomplished by many different methods, e.g. use of a Peltier device, a fan, or a coil of tubing through which refrigerant or cold liquid is circulated.

Although the heating element and temperature sensor are described herein as separate elements for convenience of describing their respective functions, embodiments are possible wherein a single element, e.g. a self-heating thermistor or resistive thermal device (RTD), can be used to enable both the heating and the temperature measurement functions.

The apparatus shown in FIG. 2, can be used to determine flow as described above (prior art). However, in a similar way it can also be used to determine the newly defined coefficient y. In order to determine the value of y a valve is provided to close the section of conduit 200 where the heat is applied and the temperature measurements are made so that a known volume of the liquid is trapped, isolated and stationary. When these conditions are provided, equation 4 can be used to calculate the coefficient y. This value is used to calibrate a thermal transfer meter, which may be located elsewhere on the conduit. In this way the thermal transfer meter can be periodically dynamically updated to accurately measure the flow of a liquid with time-varying properties. In addition to providing a means to compensate the flow measurements for any changes in the properties of the liquid, y may also be of significance in various applications. For example, when measuring urine flow in a catheter, y may have useful clinical significance as an indicator of patient health.

Consider a simple liquid conduit with liquid flowing through it from upstream to downstream. At some point the conduit can be split into two or more sub-conduits hermetically attached to the main conduit through which the liquid continues to flow. Further downstream the sub-conduits can be rejoined to again form a simple conduit. Also a mechanism can be introduced to manage the flow through the sub-conduits, such that at any given time, liquid does not have to be flowing through all of them. This is useful when it is desirable to isolate a portion of the liquid for any of various purposes, including but not limited to measuring properties of the liquid or altering properties of the isolated portion of the liquid. While some of the following examples discuss two parallel conduits, in practice any number of conduits may be used. For example, the flow may be directed through a conduit used to analyze one set of liquid properties and then directed to a second conduit for a different purpose and then to a third for maintaining the flow while the first two conduits remain closed. In similar fashion, any number of samples may be isolated while maintaining flow through the system.

Figure 3:
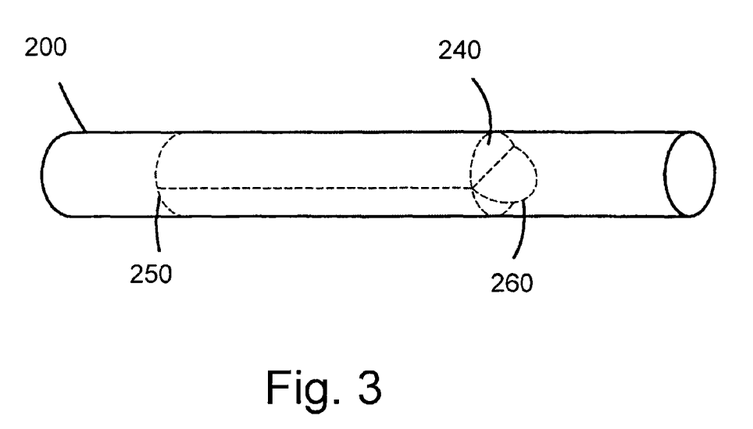
FIG. 3 schematically shows a section of a liquid conduit with a circular cross-section divided into two sub-conduits.

FIG. 3 schematically shows a section of a liquid conduit 200 with a circular cross-section. A section of the conduit is divided into an upper sub-conduit 240 and a lower sub-conduit 250. A movable flap 260 at one end of the divided section can be used to close one end of either the upper or lower sub-channels or neither one of them. When one sub-conduit is closed a known volume of liquid is trapped in it. At the same time that a quantity of liquid is trapped in one sub-conduit, the other sub-conduit is open, so the liquid can continue to flow. With this embodiment, the flap can be either at the upstream or downstream end of the sub-conduit—the flap, when closed, will trap the liquid in that sub-conduit by either preventing new liquid from entering or by preventing the trapped liquid from exiting. Of course, the two sub-channels may be in other configurations, e.g., side-by-side.

Figure 4:
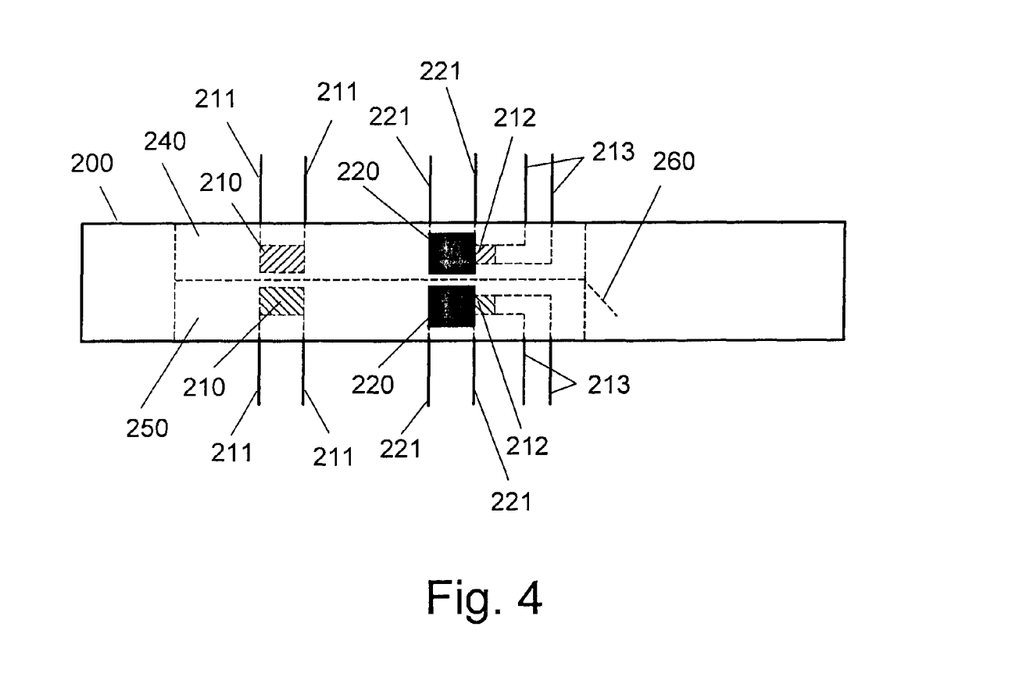
FIG. 4 schematically shows a basic embodiment of a self-calibrating thermal mass flow meter according to the present invention.

FIG. 4 schematically shows a basic embodiment of a self calibrating thermal mass flow meter according to the present invention. This embodiment employs the conduit shown in FIG. 3. The lower sub-conduit 250 will be used as the isolation chamber of known volume in which the measurements of γ will be made. Both upper sub-conduit 240 and lower sub-conduit 250 contain an arrangement of temperature sensors and heating element identical to that shown in FIG. 2. In embodiments of the invention the arrangement of temperature sensors and heating element that is located in upper sub-conduit 240 can be located at any place either upstream or downstream in the main conduit 200; however, especially if the flow rate is relatively high and/or the properties of the liquid are rapidly changing in time, the measurements in the flowing liquid and in the isolated liquid should be made physically and temporally close together to ensure accurate results.

In some applications it may be necessary to ensure that bubbles are eliminated from the liquid to ensure the conduit is full of liquid where the measurements are being made. In such an application one or more bubble traps may preferably be employed upstream of the measurement locations. Alternatively, means to allow gases to escape, such as a gas-permeable membrane may be located upstream of the measurement location.

At some conduit orientations and flow rates the conduit or sub-conduit may not be filled at the measurement location. Therefore, for some applications a check valve should be installed downstream of the measurement spot in order to create a sufficient back pressure to insure complete filling of the conduit at the location of the measurements. In some applications a check valve may be installed upstream of the measurement location, for example in order to prevent an automated system from trying to make measurements if the flow rate is below a certain value. For most applications a simple mechanical type check valve that opens when a preset pressure is exceeded is sufficient; however, in applications in which the orientation of the conduit and/or flow rate vary over a wide range of variables it is desirable to use a more sophisticated type check valve, e.g. one that is opened by a signal from a liquid level sensor in the conduit at the measurement location.

As mentioned previously, it is also possible to use the same set of heater and sensors for measuring γ when the liquid is trapped and then measuring flow when the liquid is not trapped, having taken into account any necessary re-calibration due to the measured γ. Also, in a situation where the flow can be temporarily stopped without harm, the above described system can be employed without a secondary sub-channel to maintain the flow. In situations where stopping the flow may cause harm, e.g., due to build-up of pressure, a secondary channel to maintain the flow obviates the problem.

All of the leads 211, 213, 221 are connected to a control system which comprises a processor adapted to activate the heating elements at predetermined times and voltage levels, to receive data from the temperature sensors, voltmeters, and ammeters and to use this data to determine the flow rate. The control system may also comprise means for opening and closing the flap to isolate part of the liquid, input means, e.g. a keypad, a keyboard, a touch screen, to allow a user to control parameters such as the length of time and/or quantity of heat energy that should be applied and the frequency with which the measurements are made. The control system can also comprise one or more memory units, display units, and output means to store and display to the user parameters of the system. The output means comprise communication devices that can be adapted to send the instantaneous or historical data to remote locations by using wired or wireless technologies. In addition the control system can be adapted to use the output means to send signals that provide input to other systems. For example, in an industrial setting, the signals can activate valves to cease the flow of a solution when a predetermined volume of a component has entered a mixing chamber.

In a hospital setting, the control system can be adapted to send an alarm to a nurse's station if the flow of urine from a catheterized patient to a collection bag falls below a predetermined rate, or to send an alarm if any irregularity occurs in the flow rate of a medicine being administered intravenously. When the present invention is used for urine measurement, the temperature sensors report urine temperature. By itself that may not be useful, since the urine will have cooled off on the way to the sensor, but changes in the temperature can be very meaningful—e.g., going up by a degree or two can give immediate indication of a fever, without waiting for the periodic temperature check by the staff, which may be hours later. The control system of the invention can be adapted to monitor the urine temperature and to send an alarm to the nurse's station if changes occur that exceed a predetermined rate.

Many other arrangements for isolating a portion of the flowing liquid, whether by means of stopping the flow or diverting it, are also possible as will be obvious to one trained in the art. Such arrangements can take many forms. Some examples of different embodiments will now be described. The heating elements and temperature sensors have been omitted in the description of most of the embodiments herein below; however it is to be understood that they are present and are employed mutatis mutandis in similar locations and ways as has been described in relation to FIG. 4

Figure 5A:
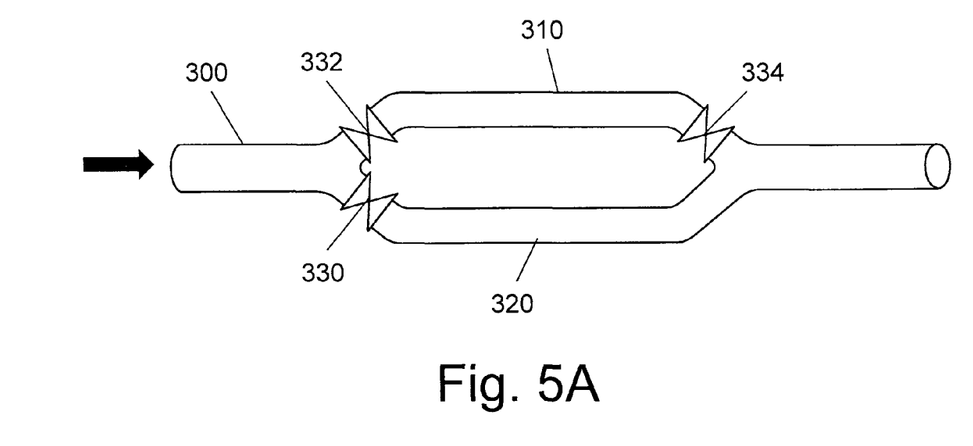
FIGS. 5A and 5B schematically illustrate an embodiment in which at a certain point the conduit bifurcates into upper branch and lower branch, which rejoin at a location downstream.
Figure 5B:
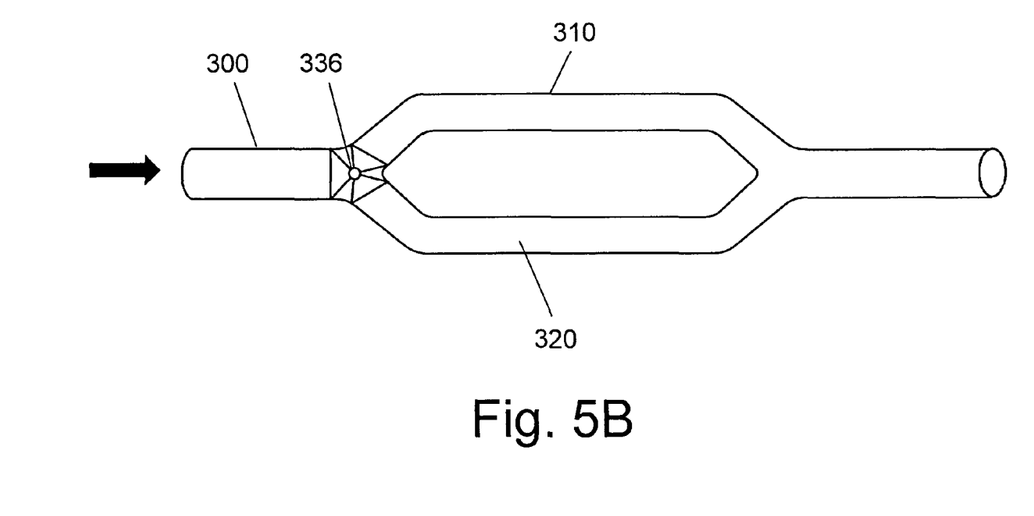

FIGS. 5A and 5B schematically illustrate an embodiment in which at a certain point the conduit 300 bifurcates into upper branch 310 and lower branch 320, which rejoin at a location downstream. One, two, or three valves may be provided as shown in FIG. 5A. If only valve 330 is present, then when it is opened liquid flowing through conduit 300 continues flowing through both branches and when valve 330 is closed liquid continuously flows through branch 310 and the liquid in branch 320 is isolated, allowing the value of γ to be measured. If both valves 330 and 332, are present then liquid can be isolated in either branch 310 or in branch 320. Valve 334 closed in conjunction with valve 332 guarantees that the liquid isolated in upper branch 310 is not in any way contacted by liquid flowing in the remainder of the system. This provides a location, i.e., in branch 310, in which to measure γ in complete isolation from the flowing liquid. In embodiments of the invention, when measurements are to be made, valve 334 can be closed first and valve 332 is closed a predetermined period later or only when sensors indicate that branch 310 is completely full with liquid. If there is a possibility that air can be in the pipe as well as liquid, an air vent to release trapped air can be located in branch 310. It is noted that when valve 334 is employed, measures may be required to account for thermal expansion, depending upon the application.

Figure 5C:
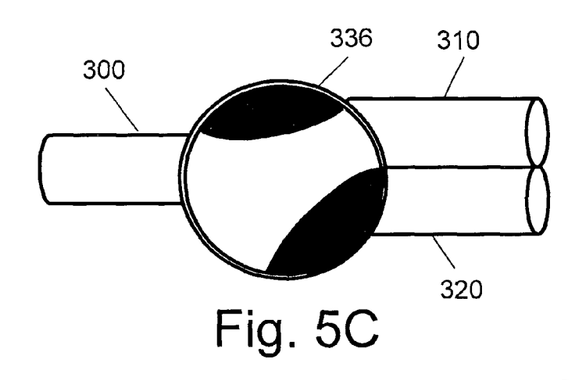
FIGS. 5C, 5D, and 5E schematically illustrate embodiments of valves that are adapted to direct the flow from a main conduit to one of a plurality of sub-conduits while blocking the flow to the remaining sub-conduits.
Figure 5D:
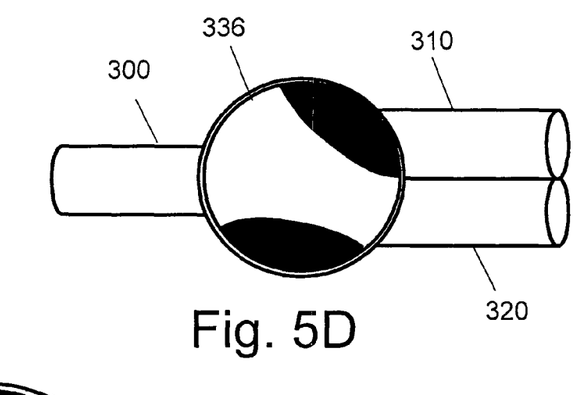

In the embodiment shown in FIG. 5B the configuration of the conduit is the same as in FIG. 5A however only one valve 336 is located in the main conduit 300 at the bifurcation. Valve 336, e.g., a rotating ball or cylindrical plug valve, is adapted to direct the flow into either one or the other of the branches 310,320 while closing the entrance to the other one, thereby isolating the liquid in it. Examples of a cross-section of valve 336 such as that described above are shown in the FIGS. 5C and 5D. Other types of multiport valves may be employed as known in the art to accomplish the same purpose.

Figure 5E:
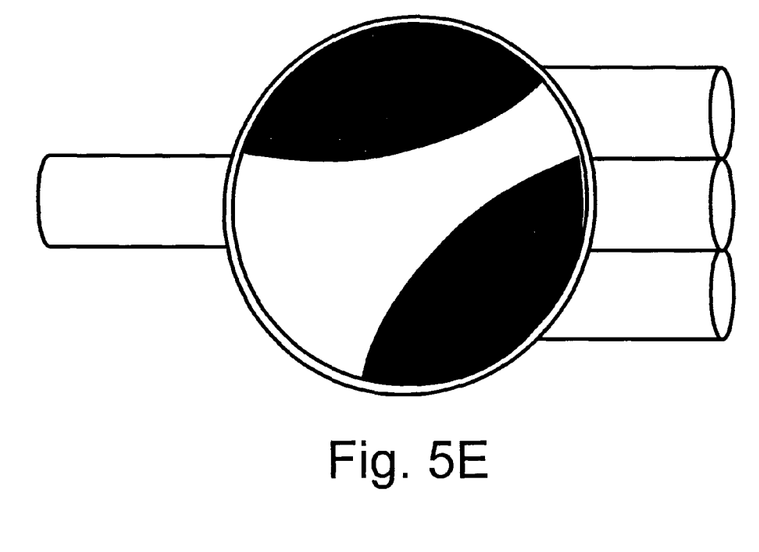

FIG. 5E schematically illustrates a valve that can be suited to directing the flow to only one out of three branches of a trifurcated channel. Many types of valves are commercially available or can be adapted by one trained in the art to meet the requirements for directing the flow from a main conduit to one of a plurality of sub-conduits while blocking the flow in the remaining sub-conduits. Multiple conduits for multiple samples are desirable when multiple types of measurements are to be made in parallel or series fashion. For example, depending on the liquid whose flow rate is being measured, sensors can be incorporated into the sub-conduits to measure some or all of the following properties of the liquid: electrical conductivity, osmolarity, osmolality, pH, biomarkers, electrolytes, specific gravity, specific density, thermal conductivity, presence and concentration of: creatinine, urea, uric acid, white blood cells, red blood cells, glucose, ketones, ions, e.g. $Na^+$, $K^+$, $Ca^{++}$, $Cl^-$.

Figure 6A:
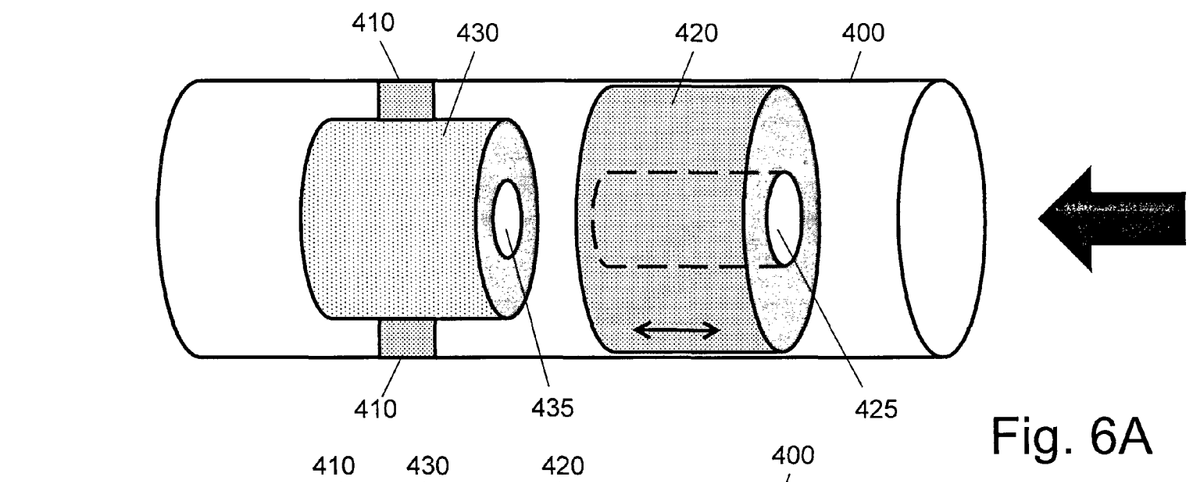
FIGS. 6A and 6B schematically illustrate another embodiment of the flow measuring apparatus of the invention.
Figure 6B:
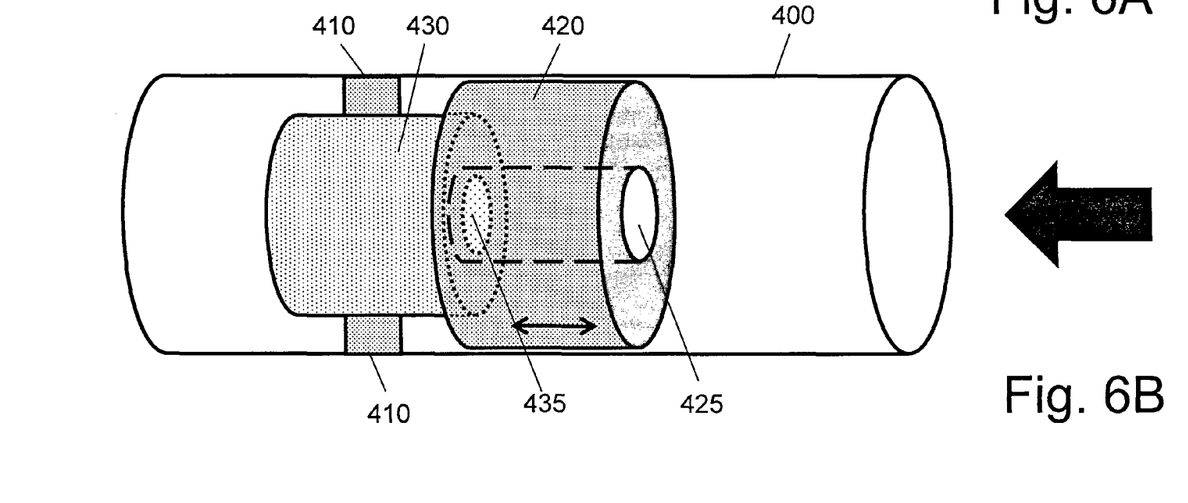

FIGS. 6A and 6B schematically illustrate another embodiment of the flow measuring apparatus of the invention. In this embodiment, liquid conduit 400 carries the liquid in the direction shown by the large arrow. Inside conduit 400 is located an inner chamber 430. Inner chamber 430 is cylindrically shaped to match the shape of conduit 400. It is hollow and is closed on the upstream side with the exception of a coaxial entrance hole that is either open or blocked by a normally closed valve 435. The inner chamber 430 is held in position by one or more supporting members 410 that are designed to hold inner chamber 430 in the correct position while offering minimal resistance to the flow of liquid around the outside of the inner chamber. Inner chamber 430 contains the heating element and temperature sensors used to make the measurements. Located inside of conduit 400 upstream of inner chamber 430 is a piston 420. Piston 420 is a solid cylinder with a coaxial hole 425 bored through its center. Piston 420 is constructed so as to allow the liquid to flow through the hole 425 but not around the piston between its outer surface and the inner surface of the wall of conduit 400. Piston 420 can be moved back and forth between the position shown in FIG. 6A and that shown in FIG. 6B. When piston 420 is in the position shown in FIG. 6B, valve 435 is open, allowing the liquid to flow through the inner chamber 430. In this configuration the flow measurements can be made. When piston 420 is in the position shown in FIG. 6A, the valve 435 is closed and the liquid flows around the outside of the inner chamber 430 while liquid that is inside the inner chamber 430 is trapped. In this configuration the measurements to determine parameter γ that is used to calibrate the flow measurement can be made. An entry valve 435 with the properties described may be constructed with a ball and spring mechanism, a spring-loaded piston, or any of the other means known in the art. The piston 420 may be moved mechanically though the use of an electric coil, e.g., solenoid, nano-motors, or other means known in the art.

Figure 7:
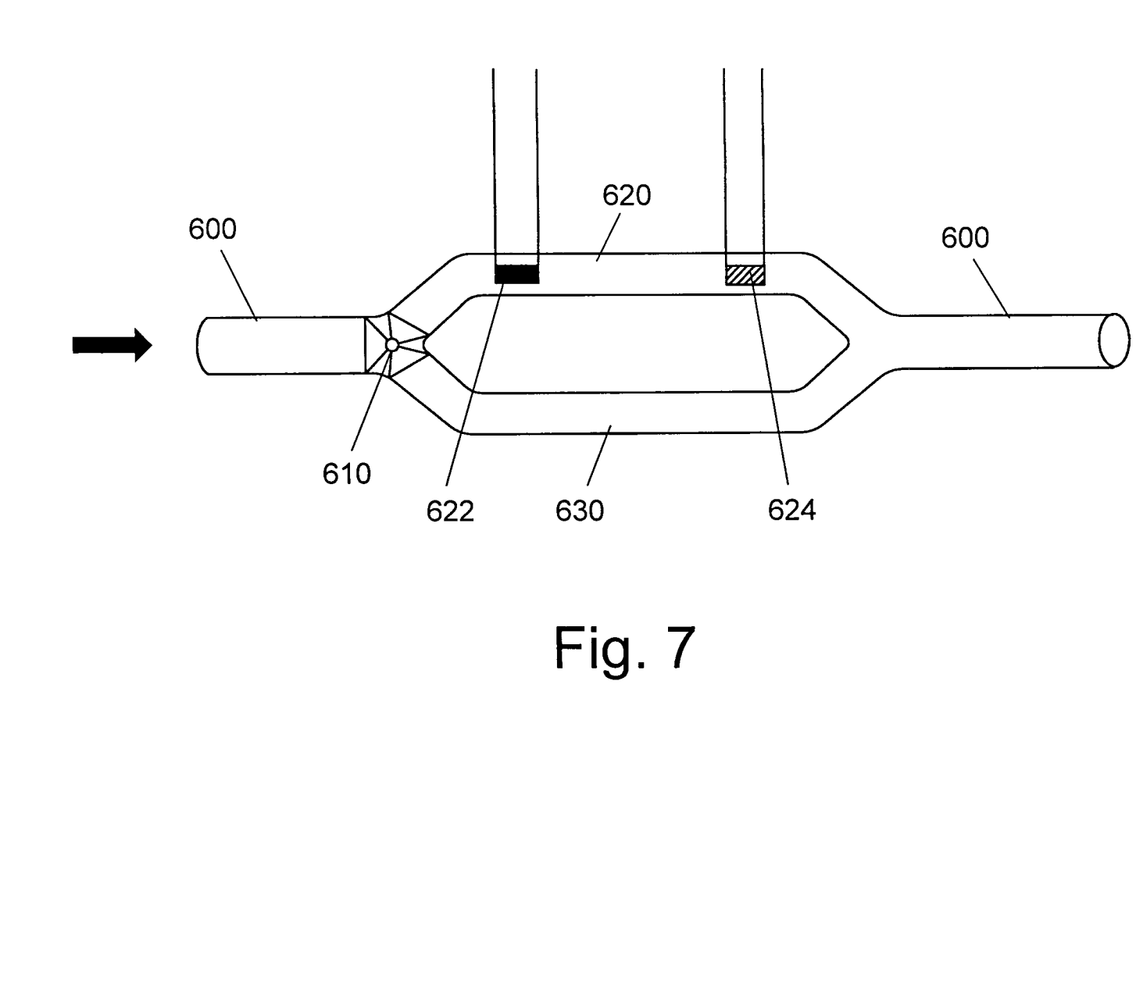
FIG. 7 schematically illustrates a method of measuring the flow rate.

FIG. 7 schematically illustrates a method of directly measuring the flow rate without the need of determining and using a value of the coefficient ν described herein above. Initially valve 610 closes branch 620 of conduit 600 trapping the liquid therein, while allowing liquid to continue to flow through branch 630. The trapped liquid in branch 620, which preferably is thermally insulated to prevent heat transfer to and from the surroundings, is at an initial temperature $T_i$ as measured by temperature sensor 624. The trapped liquid is heated by the heater 622 until a given temperature, $T_f$, is read by temperature sensor 624, The valve 610 is then reversed so that the liquid flow resumes through branch 620 and branch 630 is closed. Simultaneously a timer is started. When a temperature shift from $T_f$ back to a threshold value of temperature that may be but is not necessarily $T_i$ is measured by temperature sensor 624 the elapsed time is read from the timer. The time read, together with the known volume of the liquid displaced in branch 620 by liquid flowing into it from conduit 600 is used to calculate the sampled flow rate (volume/time). The threshold is a value that is between $T_i$ & $T_j$ that is "high enough" or "low enough" to indicate the transition of a quantity of liquid of interest. The use of a threshold is necessary because liquid doesn't get heated in a "rectangular" fashion and it may cool slightly as it flows—so the transition isn't a step function but is a gradient. For purposes of the flow calculation it is a matter of simple empirical testing depending on the application to determine the appropriate threshold to use. The threshold isn't merely a static temperature, but can also be a function of the rate of change, since different flows will affect it differently.

This method of measuring the flow rate makes it possible to keep track of the possibly changing flow rate without having to measure it continuously. Interpolation between the sample flow rates measured at different times is used to calculate the overall flow rate of the liquid through the conduit 600. The sampling process is repeated at a rate appropriate to the changing flow rate of the liquid and the accuracy requirements of the application. For example, a flow rate that changes frequently could be sampled more often, while a flow rate that changes less frequently could be sampled less often. If greater accuracy is required the flow rate can be sampled more frequently.

It is noted that according to this embodiment, the data gathered while the liquid is trapped in branch 620 can also be used to calculate γ, which may be of clinical or other interest, but is not essential to determining the flow rate, which depends entirely on the displacement of the heated (or cooled) segment of liquid by liquid at its "natural" temperature, i.e. the liquid coming afterwards, which has not been heated or cooled.

It should be noted that this method described with FIG. 7 can be applied only when the temperature of the measured liquid does not change rapidly and by large amounts. For example, when making measurements of the flow rate of urine, if the temperature goes up or down due to a fever, the incremental change introduced by the heater 622 must be sufficiently larger than that caused by the fever so that the flow measurements will be accurate. Empirical testing can be used to verify that the proper conditions for using the method are met. Such empirical methods can be, for example, when the liquid is heated in chamber 620 observing the behavior of the cooling curve and how low the temperature gets. Also monitoring the starting temperature can be used. For example if the initial temperature $T_i$ is seen to be rising over time. In general, for urine measurements the temperature will not change so rapidly that the temperature of the urine that displaces the urine heated in branch 620 would be dramatically different from initial temperature $T_i$ of the quantity of urine which was heated in the previous cycle.

Figure 8:
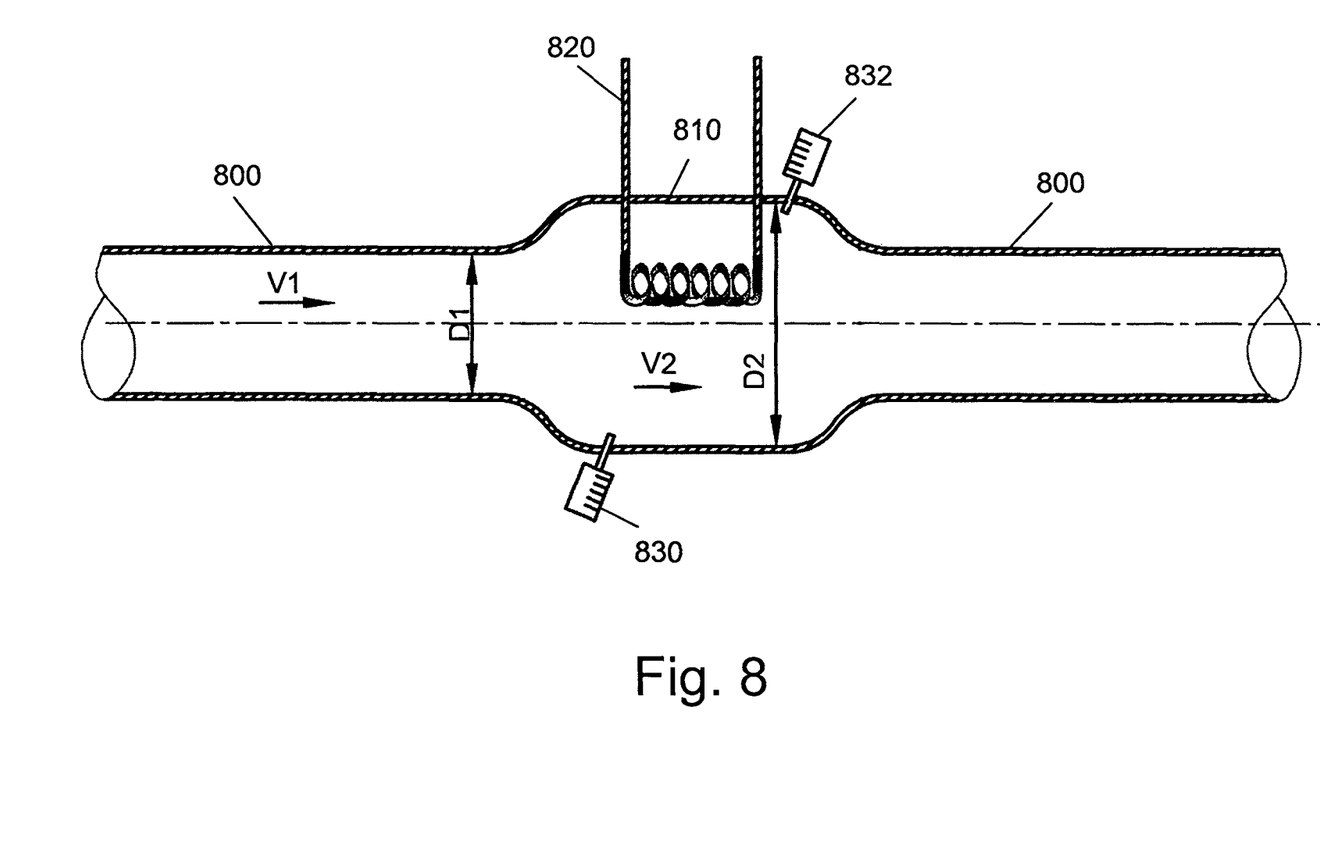
FIG. 8 schematically illustrates an embodiment of the invention wherein the flow measurements and calibration can be carried out without stopping the flow of liquid through the conduit.

As an alternative to stopping the flow completely for purposes of measuring γ, another embodiment of the invention entails slowing the velocity of the flow significantly in a region of the conduit, thus allowing the measurement to be made therein. Such an embodiment is illustrated in FIG. 8. As shown, the conduit has a small cross section segment 800 followed by a large cross section segment 810 which is followed in turn by a second small cross section segment. Also seen in the figure are heating element 820 and temperature sensors 830 and 832. For purposes of illustrating this embodiment, it is assumed the two small cross section segments are of the same diameter, D1 and the large cross section segment is of diameter D2. The conduit is configured to minimize turbulence at the transitions according to the principles known in the art and in accordance with the expected range of flow velocities to be handled. The flow velocity V2 through the large cross section segment 810 of the conduit will be slower than that of V1 through the small cross section segment 800, according to the inverse ratio of the squares of the diameters. Specifically, the velocity through the large cross section segment 810 will be in accordance with the following equation:

$$V2 = V1 \frac{D1^2}{D2^2} \qquad \text{equation 6}$$

As can be seen, the conduit can be so configured as to achieve any desired slowing down of the liquid through the large cross section segment. For example, when the large cross section segment is of a diameter one order of magnitude greater than the small cross section segment, the velocity in the large cross section segment will be two orders of magnitude slower.

For purposes of illustration, consider the example where D1 is 3 mm and D2 is 10 mm and the flow rate is 1 cc/minute. The velocity V1 will be approximately 14.15 cm/minute. According to Equation 6, the velocity V2 in the large cross section segment will be approximately 1.273 cm/minute. If D2 is increased to 15 mm, V2 is approximately 0.566 cm/min; for D2=20 mm, V2 is approximately 0.318 cc/min; and for D2=30 mm, $V_2$ is approximately 0.1415 cm/minute.

Because the large cross section segment contains a relatively very slow-moving portion of the liquid, it may be treated as a chamber in which the liquid has been isolated, while taking into account the known parameters of the configuration and the consequences thereof with respect to the flow through the chamber during the measurement therein.

The measurement of γ may be carried out in the chamber 810 so created according to the principles described above, with the following modifications: The amount of heat introduced into the chamber is a function of the time over which a pulse of energy is applied. Judicious timing of the pulse can be used to measure γ. For example, applying a short, powerful pulse will yield a corresponding raise in temperature and γ may be calculated in accordance with Equation 4, where the pulse's duration is short enough that the change in contents of the chamber is negligible. For example, in the last example cited above ($d_1$=3 mm and $d_2$=30 mm, flow rate of 1 cc/minute), and using a chamber 810 of length 10 mm, the volume of the chamber is approximately 7 $cm^3$. Every second, the volume of liquid exchanged in the chamber is approximately 0.017 $cm^3$, or less than 0.24% of the chamber volume. Thus during a pulse lasting 4 seconds or less, less than 1% of the chamber volume is exchanged. Therefore, the liquid within the chamber may be considered as standing still for an appropriately-timed measurement as described above.

As an additional consideration with regard to the previously described embodiments, while in certain applications it is preferable to have an apparatus where the flow continues unimpeded through an alternate conduit it is also possible to isolate the liquid by simply stopping the flow in a single conduit. In either case, operations may be performed on the isolated liquid in a portion of the closed conduit for the purposes of determining properties thereof and for deriving the flow rate of the liquid. The closed portion may be closed at one or both ends, depending on the needs of the application.

The above represent a few of the possible embodiments. There are many other embodiments of an apparatus to control the flow of liquid through a conduit such that one or more portions of the liquid may be isolated, as will be obvious to one trained in the art.

These embodiments can be provided as "built in" to dedicated flow lines or as separate units that can be incorporated into the flow line. For example to measure urine flow, the unit can have standard connections on both ends that allow it to be connected between the catheter and a collection bag or it may be incorporated in a catheter or in a drainage tube leading to a collection container.

Figure 9:
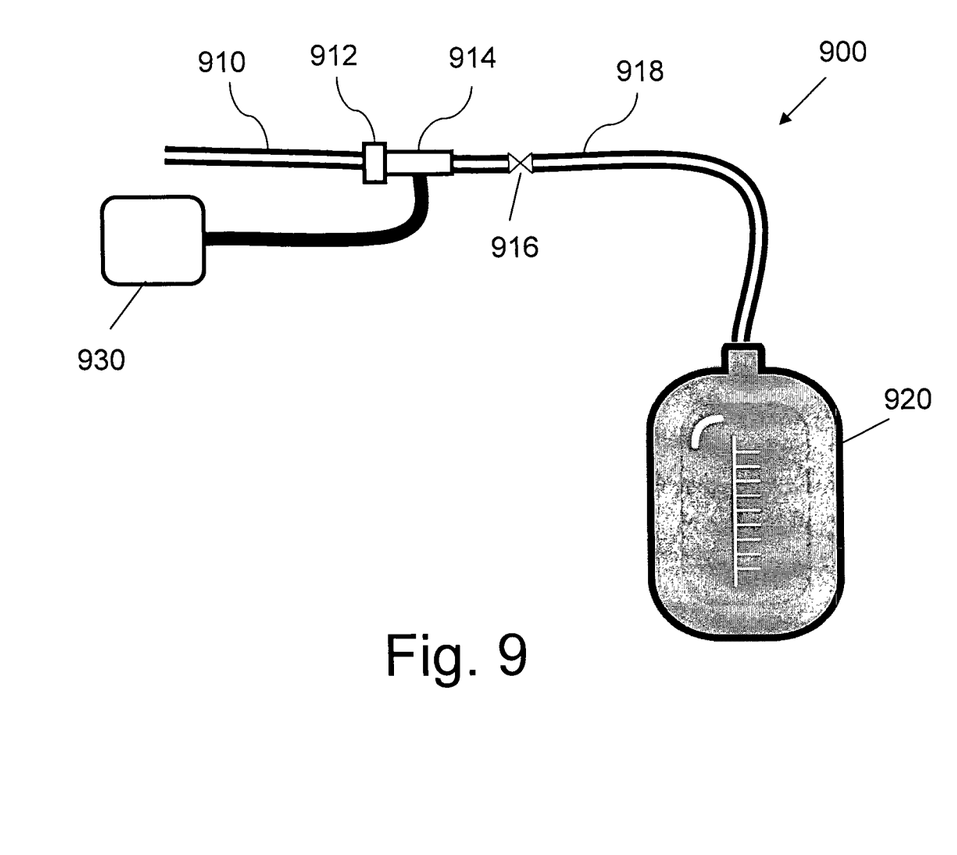
FIG. 9 schematically illustrates a system for measuring the flow of urine from a catheterized patient.

FIG. 9 schematically illustrates an embodiment of a system 900 for measuring the flow of urine from a catheterized patient (not shown in the figure). Shown in the figure are catheter 910, sensor unit 914, drain tube 918, collection bag 920, and control system 930. Optional components of system 900 are bubble trap 912 and check valve 916.

Sensor unit 914 represents the location where the measurements are made. Sensor unit 914 comprises one or more heating elements or cooling means and temperature sensors. It can be any one of the embodiments of the invention, examples of which are illustrated herein, e.g. as shown in FIGS. 2 to 8.

Control system 930 comprises input means for inputting instructions and data, software and associated circuitry for activating the heater/cooler and temperature sensors in sensor unit 914, and, optionally, software and associated electrical circuitry and components for processing data obtained from the sensor unit 914, components for displaying the results on a visual display or as audible signals or communicating them to external systems.

Although embodiments of the invention have been described by way of illustration, it will be understood that the invention may be carried out with many variations, modifications, and adaptations, without exceeding the scope of the claims.

The invention claimed is:

1. An apparatus for measuring the volumetric rate of flow of a liquid having variable values of density and/or heat capacity through a conduit, said apparatus comprising the following components:
   a) a section of said conduit adapted to form at least one chamber in which a known volume of said liquid can be isolated and either held stationary or in which the velocity of said liquid is reduced significantly in relation to its velocity in the sections of said conduit on either end of said chamber;
   b) at least one heating or cooling element adapted to add or subtract a known quantity of heat to or from said liquid; and
   c) at least one temperature sensor adapted to measure the instantaneous temperature of said liquid;
   wherein, at least one of said heating or cooling elements and at least one of said temperature sensors is in thermal contact with said known volume of said liquid that is isolated and held stationary or is flowing with a reduced velocity, thereby allowing the value of the aggregate coefficient, which is equal to the density of said liquid multiplied by the specific heat capacity of said liquid, to be determined directly said measurements of the instantaneous temperature, said known volume of liquid that is isolated and held stationary or is flowing with the reduced velocity, and said known quantities of heat that are added to or removed from said known volume of liquid that is isolated and held stationary or is flowing with the reduced velocity; and
   wherein, at least one of said heating or cooling elements and at least one of said temperature sensors is in thermal contact with said liquid that is flowing through said conduit, thereby allowing said volumetric rate of flow to be determined directly from measurements of the rate at which heat is added to or removed from said flowing liquid, measurements of the instantaneous temperature of said flowing liquid, and said volume of said aggregate coefficient, without the use of individual empirical calibration of said apparatus with said liquid.

2. The apparatus of claim 1, comprising a control system that comprises at least one of the following components: a processor, input means, memory units, display devices, and output means, wherein said components of said control system are configured to carry out at least one of the following:
   a) to activate at least one valve located in the conduit at a location at which it can be used to divert a known volume of liquid flowing in said conduit into the chamber and/or to hold said known volume of liquid stationary;
   b) to activate at least one heating or cooling element;
   c) to receive data from temperature sensors and other types of sensors or meters that are present in said apparatus;
   d) to use said received data to determine the volumetric flow rate;
   e) to store and display to a user information related to the operation of said apparatus and the properties of said liquid that are measured or determined by components of said apparatus;
   f) to send instantaneous or historical values of measured temperatures and other information relative to said liquid and said apparatus to remote locations;
   g) to send signals that can be used as input to other systems; and
   h) to send alarms if there are predetermined changes in the flow rate or other measured properties of said liquid.

3. The apparatus of claim 1, wherein the section of the conduit adapted to form at least one chamber is adapted in at least one of the following ways:
   a) by placing two valves in said conduit spaced apart by such a distance that the volume of the interior of said conduit between them defines said chamber;
   b) by splitting said conduit into at least two sub-conduits that are hermetically attached at their upstream and downstream ends to said conduit and providing a mechanism for managing the flow of liquid through said sub-conduits;
   c) by providing an inner chamber held in position inside said conduit by one or more supporting members and a piston located upstream of said inner chamber inside said conduit, wherein said piston is a solid cylinder with a coaxial hole bored through its center and said inner chamber is hollow and is closed on the upstream side with the exception of a coaxial entrance hole that is either open or blocked by a valve, which is activated by contact with said piston; and
   d) by providing a segment of conduit comprising a small cross section segment followed by a large cross section segment which is followed in turn by a second small cross section segment.

4. The apparatus of claim 3, wherein at least one of the sub-conduits comprises sensors in contact with liquid flowing through or trapped in said sub-conduit, said sensors adapted to measure at least one of the following properties of said liquid: electrical conductivity, osmolarity, osmolality, pH, biomarkers, electrolytes, specific gravity, specific density, thermal conductivity, presence and concentration of: creatinine, urea, uric acid, white blood cells, red blood cells, glucose, ketones, number/concentration of ions.

5. The apparatus of claim 1 comprising at least one of:
   a) a bubble trap located upstream of the measurement location;
   b) a gas-permeable membrane located upstream of said measurement location;
   c) a check valve located downstream of said measurement location; and
   d) a check valve located upstream of said measurement location.

6. The apparatus of claim 1, wherein said apparatus is adapted to be either connected to or an integral part of a catheter or a drainage tube leading from a patient.

7. The apparatus of claim 6, wherein urine flows through the catheter or drainage tube and the control system of said apparatus is adapted to monitor the urine temperature and to send an alarm if changes occur that exceed a predetermined rate.

8. A method for measuring the volumetric rate of flow of a liquid through a conduit, said method comprising the following steps:
   a) modifying a section of said conduit to form a chamber in which a known volume of said liquid can be isolated and either held stationary or in which the velocity of said liquid is reduced significantly in relation to its velocity in the sections of said conduit on either end of said chamber;
   b) isolating said known volume of liquid in said chamber;
   c) reading the temperature from a temperature sensor in thermal contact with said liquid in said chamber to measure an initial temperature of said liquid;
   d) activating a heating or cooling element in thermal contact with said liquid in said chamber to add or subtract a known quantity of heat to or from said isolated volume of liquid;
   e) reading the temperature from a temperature sensor in thermal contact with said liquid in said chamber to measure a final temperature of said liquid after said known quantity of heat has been added to or subtracted from said isolated volume of liquid;
   f) determining the value of an aggregate coefficient from said known volume of said liquid, said known quantity of heat, and the difference between said initial and said final temperatures;
   g) activating a thermal flow meter to measure the thermal flow rate;
   h) determining said volumetric flow rate from said measured quantity of heat, the value of said aggregate coefficient, and the difference in the temperatures measured by said first and second temperature sensors at the end of said period of time.

9. The method of claim 8, wherein the thermal flow rate is measured by:
   a) activating a heating or cooling element in thermal contact with the flowing liquid at a location either in said chamber or at another location in said conduit to add to or subtract heat from said flowing liquid;
   b) activating simultaneously with the activation of said heating or cooling element a first temperature sensor in thermal contact with said flowing liquid located upstream of said heating or cooling element and a second temperature sensor in thermal contact with said flowing liquid located downstream of said heating or cooling element;
   c) measuring the quantity of heat added to or subtracted from said flowing liquid during a period of time;
   d) determining said thermal flow rate from said measured quantity of heat and the difference in the temperatures measured by said first and second temperature sensors at the end of said period of time.

10. The method of claim 8, wherein the thermal flow rate is measured by:
   a) activating a heating or cooling element in thermal contact with the flowing liquid at a location either in said chamber or at another location in said conduit to add to or subtract heat from said flowing liquid;
   b) activating simultaneously with the activation of said heating or cooling element a temperature sensor in thermal contact with said flowing liquid and adjacent to or integral with said heating or cooling element;
   c) measuring the initial instantaneous temperature measure by said temperature sensor when it is activated;
   d) allowing the instantaneous temperature measured by said temperature sensor to rise or fall until a predetermined temperature differential between said initial temperature and the instantaneous temperature is measured;
   e) varying and measuring the amount of energy supplied to said heating or cooling element while maintaining the instantaneous temperature measured by said temperature at said temperature differential;
   f) determining the quantity of heat added to or subtracted from said flowing liquid during a period of time from said measured amount of energy;
   g) determining said thermal flow rate from said measured quantity of heat.

11. The method of claim 8, wherein step e through step f and step g are carried out simultaneously in different sections of the conduit.

12. The method of claim 8, wherein: in step d the heating or cooling element is activated and the amount of heat added to or subtracted from the isolated volume of liquid is measured, in step e the temperature is read from the temperature sensor to determine when a predetermined final temperature is reached at which point said heating or cooling element is deactivated, and in step f the value of the aggregate coefficient is determined from the known volume of liquid, the measured quantity of heat, and the predetermined difference between said initial and said final temperatures.

13. The method of claim 8, wherein steps d through h are replaced by the following steps:
   d') activating a heating or cooling element in thermal contact with said liquid in said chamber to add or subtract heat to or from said isolated volume of liquid;
   e') reading the temperature from a temperature sensor in thermal contact with said liquid in said chamber to measure the instantaneous temperature of said liquid while said quantity of heat is being added to or subtracted from said isolated volume of liquid;
   f') deactivating said heating or cooling element when the temperature of said liquid reaches a final temperature different from said initial temperature;
   g') allowing fresh liquid to flow through said chamber and activating a timer simultaneously with the time at which said fresh liquid flow is initiated;
   h') measuring the period of time that elapses until the temperature of the liquid in said chamber shifts from said final temperature back to a threshold value of temperature; and
   i') determining said volumetric flow rate from said known volume of said liquid and said measured period of time.

14. The method of claim 8, wherein said method is adapted to measure the volumetric flow of a liquid through a catheter or a drainage tube leading from a patient.

15. The method of claim 14, wherein the liquid is urine.

* * * * *